(12) United States Patent
Callegaro et al.

(10) Patent No.: US 12,168,024 B2
(45) Date of Patent: Dec. 17, 2024

(54) USE OF FUNCTIONALISED CHITOSAN IN THE TREATMENT OF INFLAMMATORY/FIBROTIC PATHOLOGIES OF THE RESPIRATORY TRACT AND HEPATIC PATHOLOGIES

(71) Applicant: GLYCOCORE PHARMA SRL, Como (IT)

(72) Inventors: Lanfranco Callegaro, Como (IT); Giulio Bianchini, Como (IT)

(73) Assignee: GLYCOCORE PHARMA, Como (IT)

( * ) Notice: Subject to any disclaimer, the term of this patent is extended or adjusted under 35 U.S.C. 154(b) by 0 days.

(21) Appl. No.: 18/556,096

(22) PCT Filed: Apr. 19, 2022

(86) PCT No.: PCT/IB2022/053638
§ 371 (c)(1),
(2) Date: Oct. 19, 2023

(87) PCT Pub. No.: WO2022/224131
PCT Pub. Date: Oct. 27, 2022

(65) Prior Publication Data
US 2024/0100084 A1 Mar. 28, 2024

(30) Foreign Application Priority Data

Apr. 22, 2021 (IT) .................. 102021000010187

(51) Int. Cl.
| | |
|---|---|
| *A61K 31/722* | (2006.01) |
| *A61K 31/136* | (2006.01) |
| *A61K 31/137* | (2006.01) |
| *A61K 31/4178* | (2006.01) |
| *A61K 31/46* | (2006.01) |
| *A61K 31/4745* | (2006.01) |
| *A61K 31/522* | (2006.01) |
| *A61K 31/573* | (2006.01) |
| *A61K 31/58* | (2006.01) |
| *A61K 47/36* | (2006.01) |
| *A61K 47/38* | (2006.01) |
| *A61P 31/14* | (2006.01) |

(52) U.S. Cl.
CPC .......... *A61K 31/722* (2013.01); *A61K 31/136* (2013.01); *A61K 31/137* (2013.01); *A61K 31/4178* (2013.01); *A61K 31/46* (2013.01); *A61K 31/4745* (2013.01); *A61K 31/522* (2013.01); *A61K 31/573* (2013.01); *A61K 31/58* (2013.01); *A61K 47/36* (2013.01); *A61K 47/38* (2013.01); *A61P 31/14* (2018.01)

(58) Field of Classification Search
CPC .. A61K 31/722; A61K 31/136; A61K 31/137; A61K 31/4178; A61K 31/46; A61K 31/4745; A61K 31/522; A61K 31/573; A61K 31/58; A61K 47/36; A61K 47/38; A61P 31/14
See application file for complete search history.

(56) References Cited

U.S. PATENT DOCUMENTS

2020/0407468 A1    12/2020   Bianchini et al.

FOREIGN PATENT DOCUMENTS

| EP | 3311823 A1 | 4/2018 |
|---|---|---|
| WO | 2017211776 A1 | 12/2017 |
| WO | 2021205294 A1 | 10/2021 |

OTHER PUBLICATIONS

D'Amelio et al., J. Phys. Chem. B, 2013, 117, p. 13578-13587. (Year: 2013).*
Henderson et al., Immunological Reviews, 2009, 230, p. 160-171. (Year: 2009).*
Vannella et al., Fibrogenesis Tissue Repair, 2008, 1, article No. 2, 11 pages. (Year: 2008).*
Search Report and Written Opinion of PCT/IB2022/053638 issued Jul. 26, 2022.

* cited by examiner

*Primary Examiner* — Jonathan S Lau
(74) *Attorney, Agent, or Firm* — Silvia Salvadori, P.C.; Silvia Salvadori

(57) ABSTRACT

The invention discloses a functionalised chitosan, or a salt thereof, used in the treatment of pathologies of the respiratory tract or hepatic pathologies, preferably caused by viral infections. It was indeed observed that said functionalised chitosan or salt thereof was able to act as galectin-modulator, modulating in particular galectin-3, and therefore determining a marked reduction in the inflammatory and fibrotic cascade generated by these viral infections. The invention moreover discloses a pharmaceutical composition, as well as a biomaterial, comprising this functionalised chitosan, or a salt thereof.

15 Claims, 2 Drawing Sheets

USE OF FUNCTIONALISED CHITOSAN IN THE TREATMENT OF INFLAMMATORY/FIBROTIC PATHOLOGIES OF THE RESPIRATORY TRACT AND HEPATIC PATHOLOGIES

This application is a U.S. national stage of PCT/IB2022/053638 filed 19 Apr. 2022, which claims priority to and the benefit of Italian Application No. 102021000010187 filed 22 Apr. 2021, the contents of which are incorporated herein by reference in their entireties.

DESCRIPTION FIELD OF THE INVENTION

The present invention concerns the use of functionalised chitosan, or a salt thereof, in the treatment of pathologies of the respiratory tract or hepatic pathologies, characterised by inflammation and/or fibrosis. Indeed, it has been observed that said functionalised chitosan or a salt thereof is able to act as a modulator of galectins, in particular galectin-3, thus determining a marked reduction in the inflammatory cascade.

The invention moreover concerns a pharmaceutical composition, as well as a biomaterial, comprising this functionalised chitosan, or a salt thereof, in the treatment of said pathologies.

BACKGROUND ART

Inflammation is a protective response by the body to invasive organisms and to lesions of the tissues. However, if unbalanced, it is often also destructive and manifests as part of the pathology in many illnesses. For this reason, there is considerable medical interest in the pharmacological modulation of inflammation. Prolonged inflammation can moreover cause fibrosis, i.e. the formation of excess fibrous connective tissue in an organ or tissue.

The fibrosis causes solidification and/or swelling of the tissues concerned and reduces the flow of fluids through these tissues. Consequently, the tissues affected by fibrosis can lose the capacity to function correctly.

Inflammatory-fibrotic pathologies of particular interest are pathologies of the respiratory tract and hepatic pathologies.

In particular, pathologies of the upper respiratory tract (for example nose, ears, nasal cavities, and throat) and of the lower respiratory tract (for example trachea, bronchi and lungs) are a serious public heath problem and one of the main causes of morbidity and mortality worldwide.

At hepatic level, when the liver is damaged repeatedly or continuously, the consequential inflammatory phenomena can cause fibrosis of the hepatic tissue that can evolve, in turn, into cirrhosis, with outcomes which can even be fatal.

Viruses are the main cause of illnesses of the respiratory tract and hepatic pathologies.

Viral infections can cause systemic damage, which can be severe. Think, for example, of the complications that arise from infection with the Sars-Cov2 virus, which is responsible for the Covid-19 pathology, mediated by what is known as a cytokine storm.

It is known, for example, that persistent viral infections concerning the respiratory tract can evolve into pulmonary fibrosis, and likewise hepatic viral infections (hepatitis) can evolve into hepatic fibrosis.

Studies have shown the important role played, on different levels, by galectins in inflammatory and fibrotic pathologies.

Galectins are a family of proteins defined by their bond specificity for β-galactosidic sugars, as well as N-acetyl-lactosamine, which can be bonded to proteins by means of N-glycosylation or O-glycosylation. At cellular level, they are able to bond with great affinity to glycoproteins containing galactose, creating associations between glycoproteins that can trigger intracellular signals and boost or modulate certain biological and pathological effects.

Incorrect regulation of the galectins, for example overexpression, is typically found in inflammatory pathologies, therefore correct regulation of these new therapies (for the treatment, the prevention, the management, and/or the improvement of the inflammatory-fibrotic pathologies of the respiratory tract and hepatic pathologies that are efficacious and either do not have or minimise side effects) is highly desirable.

Consequently, an object of the present invention is to provide a remedy for the efficacious treatment of pathologies of the respiratory tract or hepatic pathologies characterised by inflammation and/or fibrosis.

In particular, it is an object of the present invention to provide a product which is able to modulate galectins, in particular galectin-3, thereby counteracting the dysregulation of the inflammatory cascade and the pathological consequences thereof.

Moreover, recent studies have shown the fundamental role played by galectins also in viral infections.

Indeed, evolutionistic studies on coronaviruses have shown that the latter have englobed, within the S1-NTD domain of the S-glycoprotein spikes, protein sequences proper to the host cells, such as galectin receptors, in order to promote adhesion in the host cells through the recognition of glycosylated sites on the cellular surface, and therefore increase the probability of contagion. According to recent studies, the S1-NTD domain of the novel SARS-Cov2 virus, which shares the same infection mechanism as the previous SARS-CoV coronavirus, i.e. using the combination of sACE2 and TMPRSS2 receptors for recognition and entry into the host cell, includes this structural analogy.

Therefore, the novel Sars-CoV2 virus employs this infection mechanism.

The role of galectins in inflammatory and fibrotic pathologies that are consequential to viral infections is therefore still more significant.

Consequently, a further object of the present invention is to provide a remedy for the efficacious treatment of pathologies caused by viral infections, in particular pathologies of the respiratory tract and hepatic pathologies caused by viral infections and characterised by inflammation and/or fibrosis.

SUMMARY OF THE INVENTION

Said object has been achieved through the use of a functionalised chitosan, or a salt thereof, in the treatment of pathologies of the respiratory tract and hepatic pathologies, as reported in the claims annexed hereto.

In a further aspect, the present invention concerns a pharmaceutical composition comprising at least one functionalised chitosan, or salt thereof, and at least one pharmacologically active substance and/or at least one substance with a biological function, for use in the treatment of pathologies of the respiratory tract and hepatic pathologies.

BRIEF DESCRIPTION OF THE FIGURES

The characteristics and advantages of the present invention will be clear in the following detailed description and embodiments provided in the form of illustrative and non-limiting examples, as well as the annexed figures, wherein.

Figure 1:
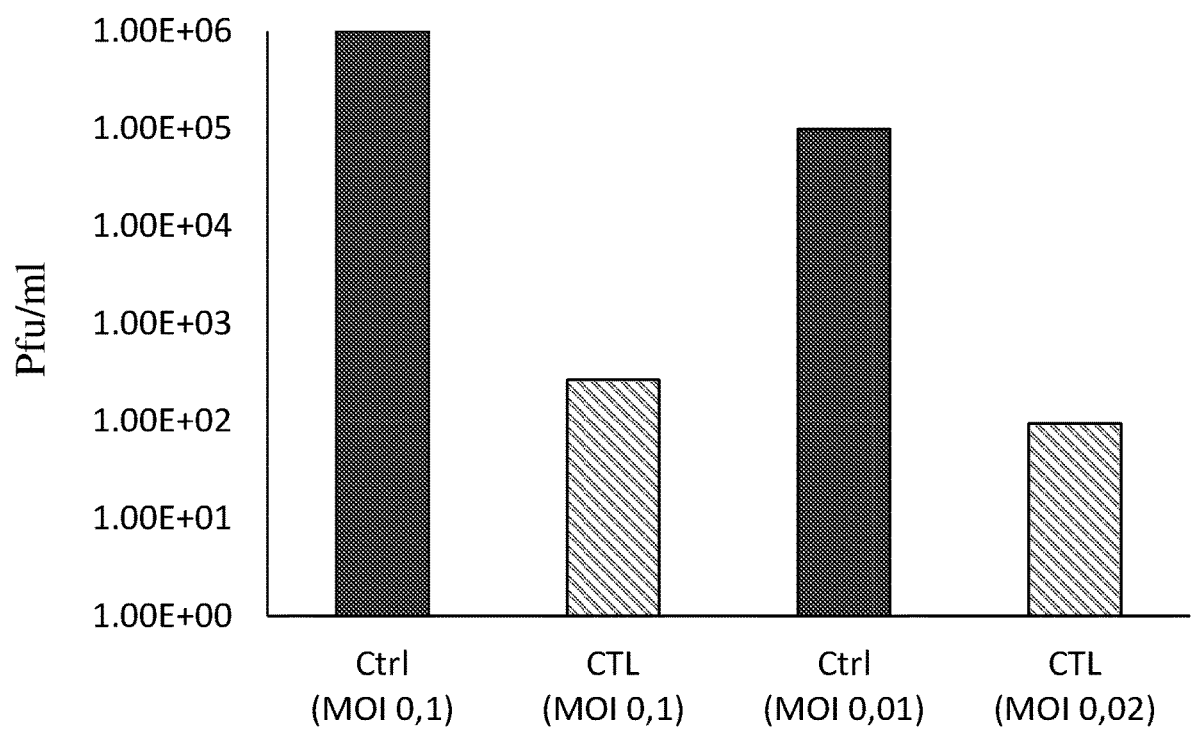
FIG. 1 shows the effect of Chitlac (CTL) on viral replication in Vero-E6 cells infected with SARS-CoV-2 at different multiplicities of infection (MOI). The reduction in infection with the virus was calculated with plaque assay. Pfu/ml=number of plaque-forming units per ml. Ctrl=cells infected with the virus in the absence of Chitlac; CTL=cells infected with the virus in the presence of 0.75 mg/ml of Chitlac.
Figure 2:
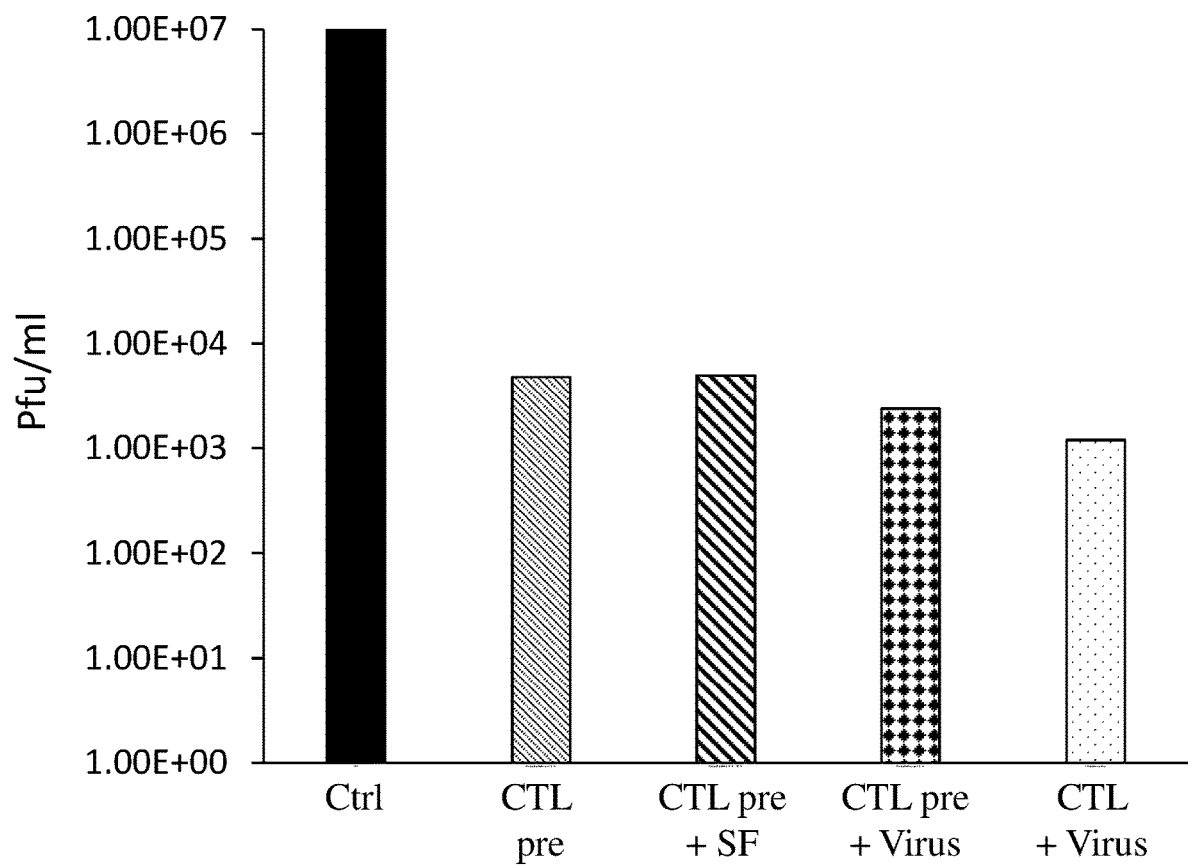

the FIG. 2 shows the effect of Chitlac (CTL) on the replication viral in Vero-E6 cells infected with SARS-CoV-2, in different culture conditions. Ctrl=cells infected with the virus in the absence of Chitlac; CTL pre=cells grown in complete DMEM and pre-treated with 0.25 mg/ml Chitlac (CTL) 30 minutes prior to infection with the virus; CTL pre+SF=cells grown in serum-free (SF) medium and pre-treated with 0.25 mg/ml CTL 30 minutes prior to infection with the virus; CTL pre+virus=cells grown in complete DMEM and infected with the pre-incubated virus with 0.25 mg/ml CTL before being added to the cell culture; CTL pre virus=cells grown in complete DMEM, infected with the virus in the presence of CTL supplemented at the time of infection. Pfu/ml=number of plaque-forming units per ml.

DETAILED DESCRIPTION OF THE INVENTION

The invention therefore concerns a functionalised chitosan, or a salt thereof, wherein at least 20% of the D-glucosamine units has formula (I):

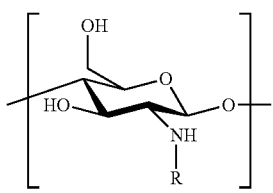

(The)

where R is a moiety of formula (1):

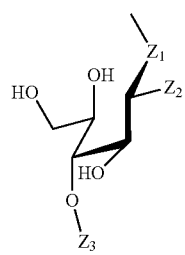

(1)

wherein $Z_1$ is —$CH_2$— or —CO—,
$Z_2$ is —OH, or —$NHCOCH_3$,
$Z_3$ is H, monosaccharide, disaccharide, or oligosaccharide, or R is a moiety of formula (2):

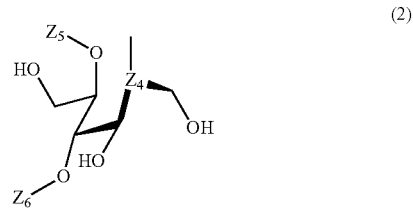

(2)

wherein $Z_4$ is —CH—,
$Z_5$ and $Z_6$ are, independently from each other, H, monosaccharide, disaccharide, or oligosaccharide,
for use as an anti-inflammatory and anti-fibrotic agent in the treatment of pathologies of the respiratory tract or hepatic pathologies, wherein said pathologies are characterised by inflammation and/or fibrosis.

For the purposes of the present invention, the term "treatment" is understood as including the administration of said functionalised chitosan, or a salt thereof, or compositions comprising said functionalised chitosan or salt thereof, to a subject suffering from said pathologies in order to improve the overall condition thereof, as well as to slow down, alleviate, reduce, and/or prevent any alteration of bodily function in said subject.

For the purposes of the present invention, the treatment of pathologies of the respiratory tract or hepatic pathologies can determine a reduction, by at least approximately 5%, 10%, 20%, 30%, 40% or even 50% or more, of the inflammatory state and/or of the fibrosis in the tissues concerned.

Inflammation and/or fibrosis of the tissues of the respiratory tract can be evaluated by monitoring any decrease in the severity, or the total disappearance, of one or more symptoms associated with the illness, or by performing biopsies and determining the marker for pulmonary function or for inflammation or fibrosis, or by means of blood gas test, bronchoscopy, X-ray, or spirometry, as known in the art.

Inflammation and/or hepatic fibrosis can be evaluated by assessing the overall wellbeing of the subject or by monitoring for any decrease in the severity, or the total disappearance, of one or more symptoms associated with the hepatic illness (for example, jaundice, fluid retention, proneness to bruising or frequent nosebleeds, condition of the skin, nails, or whites of the eyes), or by performing biopsies and determining the marker for hepatic function or for inflammation or fibrosis, or by measuring serum markers, as known in the art.

Without wishing to be bound by any theory, it is believed that the efficacy of functionalised chitosan, or a salt thereof, in the treatment of these pathologies is ascribable to the galectin-inhibiting action thereof, in particular in relation to galectin-3.

Preferably, the present invention therefore concerns a functionalised chitosan, or salt thereof, for use as an anti-inflammatory and anti-fibrotic agent in the treatment of pathologies of the respiratory tract or hepatic pathologies, wherein said pathologies are characterised by inflammation and/or fibrosis, wherein said functionalised chitosan inhibits the activity of galectin-3 at least partially.

Preferably, said pathologies of the respiratory tract or hepatic pathologies are caused by viral infections.

In particular, said viral infections are preferably ascribable to a virus selected from Syncytial Respiratory Virus, Influenza Virus, Parainfluenza Virus, Metapneumovirus, Rhinovirus, Arteriviridae, Roniviridae, Tobaniviridae, Picornaviridae, Caliciviridae, Reoviridae, Togaviridae, Toroviridae, Flaviviridae, Orthomyxoviridae, Paramyxoviridae, Rhabdoviridae, Retroviridae, Bunyaviridae, Arenaviridae, Coronaviridae, Birnaviridae, main hepatic viruses, Cytomegalovirus, Epstein-Barr virus, Coxsackievirus, and Herpes virus.

Without wishing to be bound by any theory, it is indeed believed that, owing to the recognition capacity of galectin receptors, the functionalised chitosan, or a salt thereof, can limit the infection process by inhibiting the capacity of the virus to recognise and adhere to the target cells.

For the purposes of the present invention, said pathologies of the respiratory tract or hepatic pathologies are preferably selected from asthma, pulmonary fibrosis, cystic fibrosis, hepatic fibrosis, hepatic cirrhosis, nonalcoholic steatohepatitis (NASH), viral hepatitis, chronic obstructive pulmonary disease (COPD), respiratory failure, viral infections, inflammations, interstitial pneumonia, pneumonia, pulmonary hypertension, tuberculosis, acute respiratory distress syndrome (ARDS), liver cancer, lung cancer.

Preferably, said functionalised chitosan is chitosan wherein 40-80% of the D-glucosamine units has formula (I).

Preferably, in the formula (I), $Z_3$, $Z_5$ and $Z_6$ are, independently from one another, H, moiety of glucose, galactose, arabinose, xylose, mannose, lactose, trehalose, gentiobiose, cellobiose, cellotriose, maltose, maltotriose, chitobiose, chitotriose, mannobiose, melibiose, fructose, N-acetyl glucosamine, N-acetylgalactosamine, or a combination thereof.

More preferably, $Z_3$ is H, moiety of glucose, galactose, mannose, N-acetyl glucosamine, N-acetylgalactosamine, or a combination thereof.

In particularly preferred embodiments, the moiety of formula R is a moiety of lactose or of galactose.

In certain embodiments, said functionalised chitosan is in the form of a salt thereof consisting of a cation of functionalised chitosan and a monovalent, bivalent, or trivalent anion.

Said anion is preferably selected from chloride, bromide, fluoride, iodide, acetate, trifluoroacetate, carbonate, bicarbonate, sulphate, bisulphate, C1-C10 alkylsulphate, C1-C6 alkylsulphonate, C6-C10 arylsulphonate, nitrate, hydrogen phosphate, dihydrogen phosphate, orthophosphate, oxalate, fumarate, ascorbate, citrate, gluconate, lactate, formate, tartrate, succinate, mandelate, p-toluene sulphonate, carboxylate, saccharate, benzoate, and mixtures thereof.

More preferably, the anion is chloride, bromide, acetate, sulphate, trifluoroacetate, methanesulphonate, orthophosphate, nitrate, or a mixture thereof.

In preferred embodiments, said salt is a neutral salt.

In another aspect, the present invention concerns a pharmaceutical composition comprising at least one functionalised chitosan, or a salt thereof, and at least one pharmacologically active substance and/or at least one substance with a biological function, said pharmaceutical composition being for use as an anti-inflammatory and anti-fibrotic agent in the treatment of pathologies of the respiratory tract or hepatic pathologies wherein said pathologies are characterised by inflammation and/or fibrosis.

Suitable pharmacologically active substances are antibiotic, anti-infective, antimicrobial, antiviral, cytostatic, cytotoxic, antitumoral, autoinflammatory, healing, anaesthetic, analgesic, vasoconstrictor, agonistic and antagonistic cholinergic or adrenergic, antithrombotic, anticoagulant, haemostatic, fibrinolytic, thrombolytic agents, as well as proteins and fragments thereof, peptides, polynucleotides, growth factors, enzymes, vaccines, or combinations thereof.

Preferably, said pharmacologically active substances are substances which act on the respiratory tract, for example those having a broncho-dilatating action, such as β2-adrenergic or cholinergic agonists, or xanthines, or substances with an anti-inflammatory action, or chemotherapeutical substances for tumours of the respiratory tract, corticosteroids, antileukotrienes, muscarinic antagonists, or combinations of said pharmacologically active substances.

More preferably, said pharmacologically active substances are selected from phenoterol, salbutamol, orciprenaline, ipatropium bromide, doxophylline, clenbuterol, beclomethasone, flunisolide, budesonide, irinotecan, triamcinolone, fluticasone, losartan and combinations thereof.

Preferably, said pharmacologically active substances are substances which act on the liver, for example substances with an anti-inflammatory action, corticosteroids, antioxidants such as vitamin E, silymarin, phosphatidylcholine and s-adenosyl-L-methionine, phosphodiesterase inhibitors, such as pentoxiphylline, $Na^+/H^+$ pump inhibitors, such as amiloride, a Ras antagonist, such as s-farnesylthiosalicylic acid, PPARα and PPARγ agonists, such as thiazolidinediones, renin angiotensin system inhibitors, antiviral agents, such as Lamivudine, Adefovir, Entecavir, Tenofovir, Ribavirin, sofosbuvir, angiotensin II antagonists, such as losartan, candesartan cilexetil. Preferably, said substance with a biological function is selected from hyaluronic acid, collagen, fibrinogen, fibrin, alginic acid, sodium alginate, potassium alginate, magnesium alginate, cellulose, hydroxypropyl methylcellulose, chondroitin sulphate, dermatan sulphate, keratan sulphate, heparin, heparan sulphate, laminin, fibronectin, elastin, polylactic acid, polyglycolic acid, poli (lactic-co-polyglycolic) acid, polycaprolactone, gelatine, albumin, poli(glycolide-co-caprolactone), poli(glycolide-co-trimethylene carbonate), hydroxyapatite, tricalcium phosphate, dicalcium phosphate, demineralised bone matrix, chitosan, chitin, carboxymethyl chitosan and mixtures thereof.

More preferably, said substance with a biological function is selected from hyaluronic acid, collagen, chondroitin sulphate, polylactic acid, acid poli(lactic-co-polyglycolic), elastin, a salt alginate, potassium alginate, or hydroxypropyl methylcellulose (hypromellose), combinations thereof, and combinations of said substances having a biological function with pharmacologically active substances.

Particularly preferred pharmaceutical compositions are described in the examples that follow.

Preferably, said at least one functionalised chitosan, or a salt thereof, and said at least one substance with a biological function or said pharmacologically active substance are in a weight ratio of 3000:1 to 1:3000, more preferably 100:1 to 1:150, even more preferably 50:1 to 1:75.

Preferably, the pharmaceutical composition of the invention comprises up to 10 wt % of said at least one functionalised chitosan or a salt thereof, more preferably, up to 5 wt %, based on the weight of the pharmaceutical composition. Particularly preferred are pharmaceutical compositions wherein said at least one functionalised chitosan or salt thereof amounts to 0.001-5 wt % and more preferably amounts to 0.1-1 wt %, based on the weight of the composition.

The pharmaceutical composition can further comprise pharmaceutically acceptable excipients.

Suitable pharmaceutically acceptable excipients are, for example, pH regulators, isotonic regulators, solvents, stabilisers, chelating agents, diluting agents, binding agents, disintegrating agents, lubricating agents, glidants, dyeing agents, suspending agents, surfactants, cryoprotective agents, preservative agents and antioxidant agents.

Preferably, said excipients are potassium sorbate, sodium benzoate, ε-polylysin, sucralose, maltodextrin, citric acid, sodium carbonate, calcium carbonate, magnesium carbonate, magnesium stearate, stearic acid, polyethylene glycol, natural starch, partially hydrolysed starch, modified starch, corn starch, potato starch, lactose, lactose monohydrate, calcium phosphate, calcium carbonate, calcium sulphate, polyvinylpyrrolidone, silica, colloidal silica, precipitated silica, magnesium silicates, aluminium silicates, sodium lauryl sulphate, magnesium lauryl sulphate, sodium methacrylate, sodium dehydroacetate, xanthan gum, guar gum, tara gum, locust bean gum, fenugreek gum, gum arabica, alginic acid, sodium alginate, propylene glycol alginate, sodium croscarmellose, polyvinylpolypyrrolidone, polysorbate, glyceryl-behenate, titanium dioxide, indigo carmine, cellulose, modified cellulose, calcium carboxymethylcellulose, sodium carboxymethylcellulose, microcrystalline cellulose, ethyl cellulose, gelatine, ethyl cellulose, hydroxyethyl cellulose, hydroxypropyl cellulose, polydextrose, carrageenan, methylcellulose, saccharose, saccharose esters, sorbitol, xylitol, dextrose, fructose, maltitol, tragacanth gum, pectin, agar-agar, carboxypolymethylene, hydroxypropyl methylcellulose, tragacanth, mannitol, or a mixture thereof.

Said pharmaceutical composition can be administered via inhalation, oral, intramuscular, intravenous, transdermic, sub-cutaneous, external or internal topical route, for example, surgically.

Preferably, the functionalised chitosan, as well as the pharmaceutical composition, is administered via oral, nasal or inhalation route.

In certain embodiments, the pharmaceutical composition is in a form which can be injected into the hard or soft tissues of the body, such as organs, or adipose, mucosal, or gingival tissues, preferably via intradermic, sub-cutaneous, or intramuscular route.

The functionalised chitosan, as well as the pharmaceutical composition, can be in the form of soft gel capsule or in a solid form, such as a tablet, a mini-tablet, a micro-tablet, a granule, a micro-granule, pellet, multi-particulate or micronised particulate, or powder, or in the form of a solution, emulsion, gel, ointment, drops, aerosol, or spray.

In preferred embodiments, said functionalised chitosan, as well as the pharmaceutical composition, is in the form of a powder, solution, emulsion, gel, ointment, drops, aerosol, or spray, for the administration via nasal or inhalation route.

In another aspect, the present invention concerns a biomaterial comprising at least one functionalised chitosan or a salt thereof, optionally further comprising at least one pharmacologically active substance and/or at least one substance with a biological function, for use in the treatment of pathologies of the respiratory tract or hepatic pathologies, wherein said pathologies are characterised by inflammation and/or fibrosis. Said biomaterial can be in the form of microspheres, nanospheres, a membrane, sponge, thread, film, gauze, guide channel, hydrogel, tissue, non-woven fabric, or a combination thereof.

Preferably, said biomaterial comprises up to 10 wt % of said at least one functionalised chitosan or salt thereof, more preferably, up to 7.5 wt %, based on the weight of the pharmaceutical composition. Particularly preferred are the pharmaceutical compositions wherein said at least one functionalised chitosan or salt thereof amounts to 0.001-7.5 wt %, or more preferably amounts to 0.1-1.5 wt %, or even more preferably amounts to 0.15-1.5 wt %, based on the weight of the composition.

It should be understood that the aspects stated as preferred and advantageous for the functionalised chitosan shall also be considered likewise preferred and advantageous for the preparation process, the compositions, the biomaterials, and the uses reported above.

It should also be understood that all the possible combinations of the preferred aspects of the functionalised chitosan, of the preparation process, of the compositions, of the biomaterials and of the uses stated above have also been described and are therefore likewise preferred.

EXAMPLES

Below are working examples of the present invention provided for illustrative purposes, wherein:
Examples 1-5 are examples of the preparation of neutral salts of functionalised chitosans according to the present invention;
Examples 6-23 are examples of pharmaceutical compositions comprising neutral salts of functionalised chitosans and at least one substance with a biological function or suitable excipients;
Examples 24-34 are examples of pharmaceutical compositions comprising neutral salts of functionalised chitosans and at least one pharmacologically active substance;
Examples 35-49 are examples of pharmaceutical compositions comprising neutral salts of functionalised chitosans, at least one substance with a biological function, and at least one pharmacologically active substance, and suitable excipients; and
Example 50 shows the viral replication inhibition activity of the neutral salt of functionalised chitosan according to the invention.

Example 1

Lactose (36 g), water (500 mL), acetic acid (100%) and chitosan (12 g) were loaded into a reactor and the resulting mixture heated to 60° C. for 2 hours. After which, in the same conditions, 2-methylpyridine borane (8 g) previously dispersed in methanol (80 mL) was gradually added and the system left under stirring at 60° C. for 2 hours. Next, an aqueous solution of hydrochloric acid (4 N) was added dropwise until a pH value of approximately 2 was reached. After this, the system was cooled to room temperature and the product was precipitated by adding 2-propanol. Next, the precipitated was decanted, the supernatant removed and the solid remainder washed a first time with a mixture of water:2-propanol (30:70), multiple times with mixtures of water:2-propanol (15:85) and a final time with 2-propanol. The solid was then dried in reduced pressure and controlled temperature conditions. 0.630 g neutral salt was obtained.

Example 2

0.441 g neutral salt was obtained, prepared as described in Example 1.

Example 3

0.315 g neutral salt was obtained, prepared as described in Example 1.

Example 4

0.126 g neutral salt was obtained, prepared as described in Example 1.

Example 5

Each neutral salt obtained from Examples 1-4 was dissolved in water (25 mL) and the resulting solutions were mixed at room temperature for 1 hour.

Example 6

A 0.5 N sodium hydroxide solution was added dropwise to the solution obtained in Example 5 with 0.126 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), hyaluronic acid (0.189 g), and water up to a final volume of 63 mL. The resulting mixture was stirred at room temperature until a homogeneous system was achieved. This resulted in a composition comprising the neutral salt of the functionalised chitosan and hyaluronic acid (neutral salt 0.20%, hyaluronic acid 0.30%).

Example 7

The mixture obtained in Example 6 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and hyaluronic acid (neutral salt 0.20%, hyaluronic acid 0.30%).

Example 8

A 0.5 N sodium hydroxide solution was added dropwise to the solution obtained in Example 5 with 0.126 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), non-functionalised chitosan (0.189 g), and water up to a final volume of 63 mL. The resulting mixture was stirred at room temperature until a homogeneous system was achieved. This resulted in a composition comprising the neutral salt of the functionalised chitosan and non-functionalised chitosan (neutral salt 0.20%, non-functionalised chitosan 0.30%).

Example 9

The mixture obtained in Example 8 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and non-functionalised chitosan (neutral salt 0.20%, non-functionalised chitosan 0.30%).

Example 10

A 0.5 N sodium hydroxide solution was added dropwise to the solution obtained in Example 5 with 0.315 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), polylactic acid (0.315 g), and water up to a final volume of 63 mL. The resulting mixture was stirred at room temperature until a homogeneous system was achieved. This resulted in a composition comprising the neutral salt of the functionalised chitosan and polylactic acid (neutral salt 0.50%, polylactic acid 0.50%).

Example 11

The mixture obtained in Example 10 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and polylactic acid (neutral salt 0.50%, polylactic acid 0.50%).

Example 12

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), collagen (0.630 g), and water up to a final volume of 63 mL. The resulting mixture was stirred at room temperature until a homogeneous system was achieved. This resulted in a composition comprising the neutral salt of the functionalised chitosan and collagen (neutral salt 1.00%, collagen 1.00%).

Example 13

The mixture obtained in Example 12 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and collagen (neutral salt 1.00%, collagen 1.00%).

Example 14

A 0.5 N sodium hydroxide solution was added dropwise to the solution obtained in Example 5 with 0.126 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), chondroitin sulphate (0.252 g), and water up to a final volume of 63 mL. The resulting mixture was stirred at room temperature up to the complete dissolution of the chondroitin sulphate.

This resulted in a composition comprising the neutral salt of the functionalised chitosan and chondroitin sulphate (neutral salt 0.20%, chondroitin sulphate 0.40%)

Example 15

The mixture obtained in Example 14 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and chondroitin sulphate (neutral salt 0.20%, chondroitin sulphate 0.40%).

Example 16

A 0.5 N sodium hydroxide solution was added dropwise to the solution obtained in Example 5 with 0.315 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), PLGA (0.630 g), and water up to a final volume of 63 mL. The resulting mixture was stirred at room temperature until a homogeneous system was achieved.

This resulted in a composition comprising the neutral salt of the functionalised chitosan and acid poly(lactic-co-polyglycolic) or PLGA (neutral salt 0.50%, PLGA 1.00%).

Example 17

The mixture obtained in Example 16 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and acid poly(lactic-co-polyglycolic) or PLGA (neutral salt 0.50%, PLGA 1.00%).

Example 18

A 0.5 N sodium hydroxide solution was added dropwise to the solution obtained in Example 5 with 0.126 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), elastin (0.1575 g), and water up to a final volume of 63 mL. The resulting mixture was stirred at room temperature until a homogeneous system was achieved.

This resulted in a composition comprising the neutral salt of the functionalised chitosan and elastin (neutral salt 0.20%, elastin 0.25%).

Example 19

The mixture obtained in Example 18 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and elastin (neutral salt 0.20%, elastin 0.25%).

Example 20

A 0.5 N sodium hydroxide solution was added dropwise to the solution obtained in Example 5 with 0.441 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), potassium alginate (0.473 g), and water up to a final volume of 63 mL. The resulting mixture was stirred at room temperature up to the complete dissolution of the potassium alginate. This resulted in a composition comprising the neutral salt of the functionalised chitosan and potassium alginate (neutral salt 0.70%, potassium alginate 0.75%).

Example 21

The mixture obtained in Example 20 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and potassium alginate (neutral salt 0.70%, potassium alginate 0.75%).

Example 22

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), hypromellose (0.630 g), and water up to a final volume of 63 mL. The resulting mixture was stirred at room temperature until a homogeneous system was achieved. This resulted in a composition comprising the neutral salt of the functionalised chitosan and hypromellose (neutral salt 1.00%, hypromellose 1.00%).

Example 23

The mixture obtained in Example 22 was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and hypromellose (neutral salt 1.00%, hypromellose 1.00%).

Example 24

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), phenoterol (0.00063 g), and water up to a final volume of 63 mL. The resulting mixture was stirred at room temperature until a homogeneous system was achieved. This resulted in a composition comprising the neutral salt of the functionalised chitosan and phenoterol (neutral salt 1.00%, phenoterol 0.001%).

Example 25

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), salbutamol (0.0252 g), and water up to a final volume of 63 mL. The resulting mixture was stirred at room temperature until a homogeneous system was achieved. This resulted in a composition comprising the neutral salt of the functionalised chitosan and salbutamol (neutral salt 1.00%, salbutamol 0.04%).

Example 26

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), orciprenaline (0.0315 g), and water up to a final volume of 63 mL. The resulting mixture was stirred at room temperature until a homogeneous system was achieved. This resulted in a composition comprising the neutral salt of the functionalised chitosan and orciprenaline (neutral salt 1.00%, orciprenaline 0.05%).

Example 27

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), clenbuterol (0.000252 g), and water up to a final volume of 63 mL. The resulting mixture was stirred at room temperature until a homogeneous system was achieved. This resulted in a composition comprising the neutral salt of the functionalised chitosan and clenbuterol (neutral salt 1.00%, clenbuterol 0.0004%).

Example 28

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), beclomethasone (0.0252 g), and water up to a final volume of 63 mL. The resulting mixture was stirred at room temperature until a homogeneous system was achieved. This resulted in a composition comprising the neutral salt of the functionalised chitosan and beclomethasone (neutral salt 1.00%, beclomethasone 0.04%).

Example 29

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), flunisolide (0.063 g), and water up to a final volume of 63 mL. The resulting mixture was stirred at room temperature until a homogeneous system was achieved. This resulted in a composition comprising the neutral salt of the functionalised chitosan and flunisolide (neutral salt 1.00%, flunisolide 0.10%).

Example 30

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), budesonide (0.0315 g), and water up to a final volume of 63 mL. The resulting mixture was stirred at room temperature until a homogeneous system was achieved. This resulted in a composition comprising the neutral salt of the functionalised chitosan and budesonide (neutral salt 1.00%, budesonide 0.05%).

Example 31

A 0.5 N sodium hydroxide solution was added dropwise to the solution obtained in Example 5 with 0.630 g neutral salt until pH neutral was achieved and the resulting solution was mixed for a further 30 minutes. After which, the following was added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), ipatropium bromide (0.01575 g), and water up to a final volume of 63 mL. The resulting mixture was stirred at room temperature until a homogeneous system was achieved. This resulted in a composition comprising the neutral salt of the functionalised chitosan and ipatropium bromide (neutral salt 1.00%, ipatropium bromide 0.025%).

Example 32

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), doxophylline (0.630 g), and water up to a final volume of 63 mL. The resulting mixture was stirred at room temperature until a homogeneous system was achieved. This resulted in a composition comprising the neutral salt of the functionalised chitosan and doxophylline (neutral salt 1.00%, doxophylline 1.00%).

Example 33

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), irinotecan (1.26 g), and water up to a final volume of 63 mL. The resulting mixture was stirred at room temperature until a homogeneous system was achieved. This resulted in a composition comprising the neutral salt of the functionalised chitosan and irinotecan (neutral salt 1.00%, irinotecan 2.00%)

Example 34

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), losartan (0.1575 g), and water up to a final volume of 63 mL. The resulting mixture was stirred at room temperature until a homogeneous system was achieved. This resulted in a composition comprising the neutral salt of the functionalised chitosan and losartan (neutral salt 1.00%, losartan 0.25%).

The resulting mixture was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan and losartan (neutral salt 1.00%, losartan 0.25%).

Example 35

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), phenoterolo (0.00063 g) hyaluronic acid (1.575 g), and water up to a final volume of 63 mL. The resulting mixture was stirred at room temperature until a homogeneous system was achieved. This resulted in a composition comprising the neutral salt of the functionalised chitosan, hyaluronic acid, and phenoterol (neutral salt 1.00%, hyaluronic acid 2.5%, phenoterol 0.001%).

Example 36

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), salbutamol (0.0252 g), hyaluronic acid (1.575 g), and water up to a final volume of 63 mL. The resulting mixture was stirred at room temperature until a homogeneous system was achieved. This resulted in a composition comprising the neutral salt of the functionalised chitosan, with hyaluronic acid and salbutamol (neutral salt 1.00%, hyaluronic acid 2.5%, salbutamol 0.04%).

Example 37

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), beclomethasone (0.0252 g), hyaluronic acid (1.575 g), and water up to a final volume of 63 mL. The resulting mixture was stirred at room temperature until a homogeneous system was achieved. This resulted in a composition comprising the neutral salt of the functionalised chitosan, hyaluronic acid and beclomethasone (neutral salt 1.00%, hyaluronic acid 2.5%, beclomethasone 0.04%).

Example 38

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), flunisolide (0.063 g), hyaluronic acid (1.575 g), and water up to a final volume of 63 mL. The resulting mixture was stirred at room temperature until a homogeneous system was achieved. This resulted in a composition comprising the neutral salt of the functionalised chitosan, hyaluronic acid, and flunisolide (neutral salt 1.00%, hyaluronic acid 2.5%, flunisolide 0.10%).

Example 39

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), ipatropium bromide (0.01575 g), hyaluronic acid (1.575 g), and water up to a final volume of 63 mL. The resulting mixture was stirred at room temperature until a homogeneous system was achieved. This resulted in a composition comprising the neutral salt of the functionalised chitosan, hyaluronic acid and ipatropium bromide (neutral salt 1.00%, hyaluronic acid 2.5%, ipatropium bromide 0.025%).

Example 40

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), doxophylline (0.630 g), hyaluronic acid (1.575 g), and water up to a final volume of 63 mL. The resulting mixture was stirred at room temperature until a homogeneous system was achieved. This resulted in a composition comprising the neutral salt of the functionalised chitosan, hyaluronic acid, and doxophylline (neutral salt 1.00%, hyaluronic acid 2.5%, doxophylline 1.00%).

Example 41

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), irinotecan (1.26 g), hyaluronic acid (1.575 g), and water up to a final volume of 63 mL. The resulting mixture was stirred at room temperature until a homogeneous system was achieved. This resulted in a composition comprising the neutral salt of the functionalised chitosan, hyaluronic acid and irinotecan (neutral salt 1.00%, hyaluronic acid 2.5%, irinotecan 2.00%).

Example 42

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), phenoterol (0.00063 g) hypromellose (0.630 g), and water up to a final volume of 63 mL. The resulting mixture was stirred at room temperature until a homogeneous system was achieved. This resulted in a composition comprising the neutral salt of the functionalised chitosan, hypromellose and phenoterol (neutral salt 1.00%, hypromellose 1.00%, phenoterol 0.001%).

Example 43

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), salbutamol (0.0252 g), hypromellose (0.630 g), and water up to a final volume of 63 mL. The resulting mixture was stirred at room temperature until a homogeneous system was achieved. This resulted in a composition comprising the neutral salt of the functionalised chitosan, hypromellose, and salbutamol (neutral salt 1.00%, hypromellose 1.00%, salbutamol 0.04%).

Example 44

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), beclomethasone (0.0252 g), hypromellose (0.630 g), and water up to a final volume of 63 mL. The resulting mixture was stirred at room temperature until a homogeneous system was achieved. This resulted in a composition comprising the neutral salt of the functionalised chitosan, hypromellose, and beclomethasone (neutral salt 1.00%, hypromellose 1.00%, beclomethasone 0.04%).

Example 45

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: $Na_2HPO_4$ 81 mM, $NaH_2PO_4$ 17.6 mM, NaCl 1370 mM, KCl 27 mM), flunisolide (0.063 g), hypromellose (0.630 g), and water up to a final volume of 63 mL. The resulting mixture was stirred at room temperature until a homogeneous system was achieved. This resulted in a composition comprising the neutral salt of the functionalised chitosan, hypromellose, and flunisolide (neutral salt 1.00%, hypromellose 1.00%, flunisolide 0.10%).

Example 46

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: Na$_2$HPO$_4$ 81 mM, NaH$_2$PO$_4$ 17.6 mM, NaCl 1370 mM, KCl 27 mM), ipatropium bromide (0.01575 g), hypromellose (0.630 g), and water up to a final volume of 63 mL. The resulting mixture was stirred at room temperature until a homogeneous system was achieved. This resulted in a composition comprising the neutral salt of the functionalised chitosan, hypromellose and ipatropium bromide (neutral salt 1.00%, hypromellose 1.00%, ipatropium bromide 0.025%).

Example 47

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: Na$_2$HPO$_4$ 81 mM, NaH$_2$PO$_4$ 17.6 mM, NaCl 1370 mM, KCl 27 mM), doxophylline (0.630 g), hypromellose (0.630 g), and water up to a final volume of 63 mL. The resulting mixture was stirred at room temperature until a homogeneous system was achieved. This resulted in a composition comprising the neutral salt of the functionalised chitosan, hypromellose, and doxophylline (neutral salt 1.00%, hypromellose 1.00%, doxophylline 1.00%).

Example 48

A 0.5 N sodium hydroxide solution was added dropwise to the solution obtained in Example 5 with 0.630 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: Na$_2$HPO$_4$ 81 mM, NaH$_2$PO$_4$ 17.6 mM, NaCl 1370 mM, KCl 27 mM), g), irinotecan (1.26 g), hypromellose (0.630 g), and water up to a final volume of 63 mL. The resulting mixture was stirred at room temperature until a homogeneous system was achieved. This resulted in a composition comprising the neutral salt of the functionalised chitosan, hypromellose, and irinotecan (neutral salt 1.00%, hypromellose 1.00%, irinotecan 2.00%).

Example 49

A 0.5 N sodium hydroxide solution was added dropwise to the solution obtained in Example 5 with 0.126 g neutral salt until pH neutral was achieved and the resulting solution was mixed for a further 30 minutes. After this, the following were added in the same conditions and in the following order: a 10×PBS solution with a final osmolarity within a range of 250-350 mOSm/l (PBS 10×: Na$_2$HPO$_4$ 81 mM, NaH$_2$PO$_4$ 17.6 mM, NaCl 1370 mM, KCl 27 mM), losartan (0.1575 g), non-functionalised chitosan (0.189 g), and water up to a final volume of 63 mL. The resulting mixture was stirred at room temperature until a homogeneous system was achieved. This resulted in a composition comprising the neutral salt of the functionalised chitosan, non-functionalised chitosan, and losartan (neutral salt 0.20%, 0.30%, 0.25%).

The resulting mixture was frozen at −80° C. for one night. The following day, it was placed in the freeze dryer at approximately 50 mbar and −50° C. for 24 hours. Once the powder had been obtained, this was ground/sieved to obtain the desired particle size and supplemented with the excipients to produce a pharmaceutical solid form. This resulted in a composition comprising the neutral salt of the functionalised chitosan, non-functionalised chitosan and losartan (neutral salt 1.00%, 0.30%, 0.25%).

Example 50

Viral replication inhibition by the neutral salt of the functionalised chitosan according to the invention (Chitlac) was tested in cells infected with SARS-CoV-2, and the number of plaque-forming units was evaluated.

First and foremost, 250,000 Vero E-6 cells were infected with the SARS-CoV-2 virus at a multiplicity of infection (MOI) of 0.1 and of 0.01, in the presence or absence of Chitlac.

After an hour of incubation, the virus was removed and DMEM was added to the cells, containing the 2% (v/v) serum and 0.75% (p/v) carboxymethylcellulose.

The infected cells were then placed in an incubator with 5% (v/v) C02 at 37° C.±1° C. and subsequently observed under an optical microscope to detect the formation of plaques which have undergone lysis as a result of the cytopathic effect (CPE) of the viral suspension. We then counted said cells, after fixing them with formaldehyde and staining them with a crystal violet solution.

The effect of Chitlac on viral replication was then tested. FIG. 1 shows the results obtained with cells grown in complete DMEM and infected with different multiplicities of infection (MOI), in the presence or absence of 0.75 mg/ml Chitlac (CTL). The reduction in viral infection was calculated by plaque-forming assay. Pfu/ml=number of plaque-forming units per ml. Ctrl=cells treated with the Virus in the absence of CTL. The experiment showed an evident reduction in viral replication in the presence of CTL. FIG. 2 shows the results obtained in different conditions: the cells were grown in complete DMEM or serum-free (SF) medium, then infected. Chitlac (CTL) at a concentration of 0.25 mg/ml was added 30 minutes prior to infection with the virus (CTL pre and CTL pre+SF in FIG. 2); or the cells were infected with a pre-incubated virus in 0.25 mg/ml of Chitlac, before being added to the cell culture (CTL pre+Virus in FIG. 2), or still further, the cells were infected with the virus in the presence of Chitlac supplemented at the time of infection (CTL+Virus in FIG. 2). In all the cases, the treatment with Chitlac determined a reduction in the plaque-forming units per ml, thus demonstrating the inhibitory activity of Chitlac on viral replication. Chitlac can therefore be used to treat or prevent viral infections.

The invention claimed is:

1. A method of treating pathologies of the respiratory tract or hepatic pathologies, wherein said pathologies are characterized by inflammation and/or fibrosis, the method comprising the step of administering to a subject in need thereof an effective amount of a functionalized chitosan, or a salt thereof, as anti-inflammatory and anti-fibrotic agent, said functionalized chitosan being a chitosan wherein at least 20% of D-glucosamine units have the formula (I):

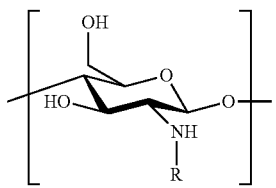

where R is a moiety of formula (1):

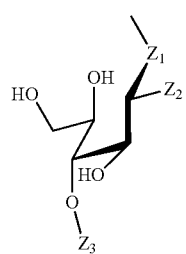

wherein $Z_1$ is —CH2— or —CO—,
$Z_2$ is —OH, or —NHCOCH$_3$,
$Z_3$ is H, monosaccharide, disaccharide, or oligosaccharide,
or R is a moiety of formula (2):

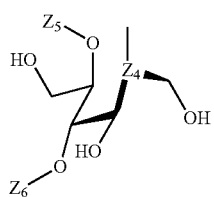

wherein $Z_4$ is —CH—,
$Z_5$ and $Z_6$ are, independently of each other, H, monosaccharide, disaccharide, or oligosaccharide.

2. The method of claim 1, wherein said functionalized chitosan at least partially inhibits activity of galectin-3.

3. The method of claim 1, said functionalized chitosan being in the form of its salt consisting of functionalized chitosan cation and monovalent, bivalent or trivalent anion.

4. The method of claim 1, wherein said functionalized chitosan is chitosan wherein 40-80% of D-glucosamine units have the formula (I).

5. The method of claim 1, wherein, in said functionalized chitosan, $Z_3$, $Z_5$ and $Z_6$ are, independently of one another, H, residue of glucose, galactose, arabinose, xylose, mannose, lactose, trehalose, gentiobiose, cellobiose, cellotriose, maltose, maltotriose, chitobiose, chitotriose, mannobiose, melibiose, fructose, N-acetyl glucosamine, N-acetyl galactosamine, or combinations thereof.

6. The method of claim 1, wherein, in said functionalized chitosan, $Z_3$ is H, residue of glucose, galactose, mannose, N-acetyl glucosamine, N-acetyl galactosamine, or combinations thereof.

7. The method of claim 1, wherein, in said functionalized chitosan, R is a residue of lactose or galactose.

8. The method of claim 1, wherein said functionalized chitosan is administered in the form of a pharmaceutical composition, said composition comprising at least one functionalized chitosan of claim 1, and at least one pharmacologically active substance and/or at least one substance having a biological function, wherein:
said pharmacologically active substance is selected from antibiotics, anti-infectives, antimicrobials, antivirals, cytostatic, cytotoxic, antitumor, anti-inflammatory, cicatrizers, anesthetic, analgesic, vasoconstrictors, cholinergic or adrenergic agonists and antagonists, antithrombotic, anticoagulant, hemostatic and fragments thereof, peptides, polynucleotides, growth factors, enzymes, vaccines, and combinations thereof, and
said substance having a biological function is selected from hyaluronic acid, collagen, fibrinogen, fibrin, alginic acid, sodium alginate, potassium alginate, magnesium alginate, cellulose, hydroxypropylmethylcellulose chondroitin sulfate, dermatan sulfate, keratan sulfate, heparin, heparan sulfate, laminin, fibronectin, elastin, polylactic acid, polyglycolic acid, poly (lactic-co-glycolic acid), polycaprolactone, gelatin, albumin, poly (glycolide-co-caprolactone), poly(glycolide-co-trimethylene carbonate), hydroxyapatite, tricalcium phosphate, dicalcium phosphate, demineralized bone matrix, chitosan, chitin, carboxymethyl chitosan, and mixtures thereof.

9. The method of claim 8, wherein, in said pharmaceutical composition:
said pharmacologically active substance is selected from fenoterol, salbutamol, orciprenaline, ipatropium bromide, doxoflllin, clenbuterol, beclomethasone, flunisolide, budesonide, irinotecan, triamcinolone, fluticasone, losartan or combinations thereof;
said substance having a biological function is selected from hyaluronic acid, collagen, chondroitin sulfate, polylactic acid, poly (lactic-co-glycolic) acid, elastin, potassium alginate or hydroxypropylmethylcellulose, or combinations thereof.

10. The method of claim 8, wherein, in said pharmaceutical composition, said functionalized chitosan, or a salt thereof, is in an amount of 0.001-5% by weight on the weight of the composition.

11. The method of claim 10, wherein, in said pharmaceutical composition, said functionalized chitosan, or a salt thereof, is in an amount of 0.1-1% by weight on the weight of the composition.

12. The method of claim 1, wherein said functionalized chitosan is administered in the form of a biomaterial, said biomaterial comprising at least one functionalized chitosan, or a salt thereof, of claim 1, and optionally further comprising at least one pharmacologically active substance and/or at least one substance having a biological function.

13. The method of claim 1 wherein said pathologies of the respiratory tract or hepatic pathologies are caused by viral infections.

14. The method of claim 1 wherein said pathologies of the respiratory tract or hepatic pathologies are caused by viral infections attributable to a virus selected from: Respiratory Syncytial Virus, Influenza Virus, Parainfluenza Virus, Metapneumovirus, Rhinovirus, Arteriviridae, Roniviridae, Tobaniviridae, Picornaviridae, Caliciviridae, Flaviridae, Togoviridae, Paramyxoviridae, Rhabdoviridae, Retroviridae, Bunyaviridae, Arenaviridae, Coronaviridae, Birnaviridae, Major hepatic viruses, Cytomegalovirus, Epstein-Barr virus, Coxsackie virus and Herpesvirus.

15. The method of claim 1, wherein said pathologies of the respiratory tract or hepatic pathologies are selected from asthma, pulmonary fibrosis, cystic fibrosis, liver fibrosis, liver cirrhosis, chronic obstructive pulmonary disease (COPD), respiratory failure, viral infections, inflammation, interstitial pneumonia, pneumonia, pulmonary hypertension, tuberculosis, ARDS, lung cancer and liver cancer.

\* \* \* \* \*